US007259012B2

(12) United States Patent
Lotteau et al.

(10) Patent No.: US 7,259,012 B2
(45) Date of Patent: *Aug. 21, 2007

(54) USE OF OXIDIZED LIPOPROTEINS FOR DIFFERENTIATION OF PRECURSOR CELLS INTO MATURE DENDRITIC CELLS

(75) Inventors: Vincent Lotteau, Vourles (FR); Patrice Andre, Lyons (FR)

(73) Assignees: Biomerieux, Marcy l'Etoile (FR); Institut National de la Sante et de la Recherche Medicale, Paris (FR)

( * ) Notice: Subject to any disclaimer, the term of this patent is extended or adjusted under 35 U.S.C. 154(b) by 340 days.

This patent is subject to a terminal disclaimer.

(21) Appl. No.: 10/482,480

(22) PCT Filed: Jul. 8, 2002

(86) PCT No.: PCT/FR02/02390

§ 371 (c)(1),
(2), (4) Date: Feb. 18, 2004

(87) PCT Pub. No.: WO03/006634

PCT Pub. Date: Jan. 23, 2003

(65) Prior Publication Data

US 2004/0219672 A1     Nov. 4, 2004

(30) Foreign Application Priority Data

Jul. 9, 2001      (FR) .................................. 01 09103

(51) Int. Cl.
*C12N 5/00* (2006.01)
*C12N 5/06* (2006.01)
*C12N 5/08* (2006.01)
*A61K 47/44* (2006.01)

(52) U.S. Cl. ...................... 435/373; 435/372; 435/377; 424/283.1; 424/93.7

(58) Field of Classification Search ................ 435/373, 435/377, 372; 424/283.1, 93.7
See application file for complete search history.

(56) References Cited

U.S. PATENT DOCUMENTS 5,776,978 A * 7/1998 Bruzzese .................... 514/558
5,998,452 A * 12/1999 Ohi et al. ................... 514/369
6,039,946 A * 3/2000 Strahilevitz .............. 424/140.1

OTHER PUBLICATIONS

Perrin-Cocon et al, "Oxidized low Density Lipoprotein Promotes mature Dendritic Cell Transition from Differentiating Monocytes", J. Immunology, Oct. 2001; 167(7):3785-91.*
Hamilton et al, "Oxidized LDL Can Promote Human Monocyte Survival", Arterioscler. Thromb. Vasc, Biol., 2000; 20;2329-2331.*

* cited by examiner

*Primary Examiner*—Ruth A Davis
(74) *Attorney, Agent, or Firm*—Oliff & Berridge, PLC

(57) ABSTRACT

The invention concerns a method for differentiating precursor cells into mature dendritic cells, comprising placing the precursor cells in a medium suitable for their differentiation and adding to the medium, in a predetermined amount, at least one fraction of oxidized lipoproteins selected among oxidized very low density lipoproteins (VLDLs) and/or oxidized intermediate density lipoproteins (IDLs) and/or oxidized low density lipoproteins (LDLs). The precursor cells are preferably monocytes.

20 Claims, No Drawings

USE OF OXIDIZED LIPOPROTEINS FOR DIFFERENTIATION OF PRECURSOR CELLS INTO MATURE DENDRITIC CELLS

The present invention relates to the use of at least one fraction of oxidized lipoproteins chosen from oxidized VLDLs and/or oxidized IDLs and/or oxidized LDLs, for the differentiation of precursor cells, in particular of monocytes, into mature dendritic cells.

Dendritic cells are involved in the development of an immune response and in the initiation of a specific T lymphocyte response, by recognition, capture and presentation of antigens, in particular of infectious agents (Steinman et al. 1997, Immuno. Rev., 156: 25-37; Cella et al. 1997, Curr. Opin. Immunol., 9: 10-16).

Immature dendritic cells are located in non-lymphoid tissues. These cells are also called Langerhans cells when they are located in the skin, and in all the epidermides outside the intestine. Dendritic cells, in smaller amounts, are also located in organs such as the liver, the lung and the intestine. These immature dendritic cells capture and digest the antigens of infectious agents in a very efficient manner.

While dendritic cells exist in the immature state in most tissues, certain signals, such as bacterial agents or inflammatory cytokines, can activate them by inducing a process of maturation. Dendritic cell activation is the initial step in triggering the adaptive immune response. Specifically, during this activation, dendritic cells acquire the ability to migrate to the lymphoid organs, where T lymphocytes are found, and the ability to transmit costimulation signals which are essential to the activation of naïve T lymphocytes. Thus, during the migration of dendritic cells to the lymphoid organs, the dendritic cells undergo functional and phenotypic modifications which are grouped together under the term maturation, which is characterized by:
1) an increase at the dendritic cell surface of molecules involved in T lymphocyte activation (such as CD40, CD80, CD83 and CD86, and the class I and II major histocompatibility complex (MHC) molecules;
2) the production of pro-inflammatory cytokines (such as the interleukins IL-12, IL-1β and IL-6);
3) a decrease in the ability of dendritic cells to capture and digest the antigen.

By virtue of their abilities to develop an immune response and to initiate a specific T lymphocyte response, dendritic cells are of particular therapeutic interest, in particular in the fields of immunization against infections and antitumor immunization, and of immunotherapy (Austin. 1998, Curr. Opin. Hematol. 5:3-15; Reise Sousa et al. 1999, Curr. Opin. Immunol. 11: 392-399).

In vivo, monocytes are circulating cells which can penetrate into tissues. By crossing the vascular endothelial wall, monocytes come into contact with environmental factors which influence what becomes of them. Schematically, three possibilities are envisioned for these cells: 1) departure from the tissues and return to the lymph nodes, 2) differentiation into macrophages, 3) differentiation into immature dendritic cells. The nature of the endogenous environmental factors which direct the monocytes toward one or other of these pathways is still unknown.

In vitro, the first step for obtaining mature dendritic cells from monocytes is induction of the differentiation of monocytes in culture into immature dendritic cells with in particular the interleukin IL-4 and the factor GM-CSF (Granulocyte Macrophage-Stimulating factor). After 6 days, 95% of the cells in culture are immature dendritic cells. The second step is activation of the maturation of the immature dendritic cells, which is generally induced with exogenous agents, such as bacterial or viral agents or any other molecules capable of inducing maturation. It has thus been described, by Pascale Jeannin et al. (Nature Immunology, 2000, 1: 502-509) that the kpOmpA protein from *Klebsiella pneumoniae*, added to immature dendritic cells on the 6th day of culturing is capable of inducing maturation of these cells. As a variant of the second step, mention may be made of application WO-A-97/29182, which describes the addition, to the culture medium for 3 days, of a conditioned medium comprising a dendritic cell maturation factor, such as gamma-globulin or a bacterial agent from *Staphylococcus aureus* (pansorbin), so as to obtain dendritic cell maturation.

It can thus be seen that the period of time for obtaining mature dendritic cells is substantially long since it requires at least 6 days to reach to the state of immature dendritic cells and at least 2 days for their maturation.

Moreover, the use of exogenous molecules derived from infectious agents for initiating dendritic cell maturation is difficult to envision in the context of vaccinology and immunotherapy, due to the problems of safety and cost associated with the use of infectious agents (direct or indirect side effects in vivo; very important need for purification according to very strict legal or regulatory requirements).

The invention proposes to respond to all the disadvantages of the state of the art by, firstly, decreasing the amount of time required for obtaining mature dendritic cells and, secondly, avoiding the use of exogenous molecules derived from infectious agents for activating the maturation. Surprisingly, the inventors have demonstrated that oxidized lipoproteins, in particular oxidized LDLs (oxidized Low Density Lipoproteins), permit the differentiation of precursor cells, such as in particular monocytes in culture, into cells exhibiting the morphological and phenotypic characteristics of mature dendritic cells. Lipoproteins are water-soluble spherical particles which transport nonpolar lipids. In humans, LDLs are the main cholesterol transporters and are made up of a hydrophobic core containing cholesterol ester molecules, and an envelope made up of a layer of polar lipids (mainly phospholipids) into which is inserted apolipoprotein B. Plasma LDLs can cross the endothelium and undergo oxidative modifications, in particular in the subendothelial space (Witztum et al. 1991, J. Clin. Invest., 88: 1785-1792; Steinberg et al. 1988, In *atherosclerosis reviews*. Raven Press, NY, 1-23). Oxidized LDLs exhibit inflammatory activities. The pro-inflammatory oxidative modifications of LDLs are under the control of native LDLs and of native HDLs (High Density Lipoproteins). It has in particular been shown that the enzymes paraoxonase and platelet-activating factor acetylhydrolase (or PAF-AH) prevent, under normal conditions, the accumulation of oxidized LDLs (Mackness et al. 1991, FEBS Lett., 286: 152-154; Watson et al. 1995, J. Clin. Invest. 96: 2882-2891; Watson et al., 1995, J. Clin. Invest. 95: 774-782). During the acute phase of an attack, considerable modifications appear in the plasma, and in particular in the composition of the lipoproteins. For example, the composition of the HDLs varies, resulting in conversion of anti-inflammatory HDLs to pro-inflammatory HDLs. Oxidized LDLs stimulate in particular the expression of MCP-1 (Monocyte Chemoattractant Protein-1), M-CSF (Macrophage Colony-Stimulating Factor) and GM-CSF (Granulocyte Macrophage Colony-stimulating factor) by endothelial cells and increase the adhesion of monocytes and their transmigration across endothelial cells (Kruth, 1985, Atherosclerosis, 57: 337-341; Simionescu et al, 1986, Am. J. Pathol., 123: 109-125; Frank et al. 1989, J. Lipid Res., 30: 967-978; Rajavashisth et al. 1990, Nature, 344: 254-257; Navab et al. 1991, J. Clin. Invest., 88: 2039-2046).

To date, no element of the prior art either describes or suggests the differentiation of precursor cells, such as in particular monocytes, into mature dendritic cells in the presence of oxidized LDLs.

Thus, the present invention relates to the use of at least one fraction of oxidized lipoproteins chosen from oxidized VLDLs (Very Low Density Lipoproteins) and/or oxidized IDLs (Intermediate Density Lipoproteins) and/or oxidized LDLs (Low Density Lipoproteins), for the differentiation of precursor cells into mature dendritic cells. The term "precursor cells" is intended to means cells capable of differentiating into dendritic cells, such as in particular monocytes or CD34+ cells, isolated in particular from cord blood or bone marrow. The term "precursor cells" is also intended to mean pluripotent cells or immature cells with the ability to differentiate into immature and mature dendritic cells. They may be cells which have been isolated and purified or cell lines cultured in vitro. In one embodiment of the invention, the precursor cells differentiate into immature dendritic cells in the presence of IL-4 and of GM-CSF. According to a preferred embodiment of the invention, the precursor cells are monocytes. In a preferred embodiment of the invention, the monocytes are isolated from human peripheral blood. According to other embodiments, the monocytes are isolated from mice, from rats, from rabbits, from monkeys or from any other mammal.

According to a preferred embodiment of the invention, the differentiation of the monocytes into mature dendritic cells is carried out in vitro.

The fractions are obtained from centrifugation of plasma according to a conventional protocol known to those skilled in the art, and are defined by their density: density less than 1.0063 g/ml for the VLDL fraction, density of between 1.025 and 1.0063 g/ml for the IDLs and density of between approximately 1.06 and 1.025 g/ml for the LDLs, preferably between 1.055 and 1.025 g/ml.

The present invention also relates to the use of at least one fraction of oxidized lipoproteins chosen from oxidized VLDLs and/or oxidized IDLs and/or oxidized LDLs, for producing a medicinal product intended to produce the differentiation of precursor cells, in particular of monocytes, into mature dendritic cells.

According to a preferred embodiment of the invention, this medicinal product may be used for the production of mature dendritic cells after bringing into contact with a biological agent. By virtue of this medicinal product, mature dendritic cells presenting a given antigen are obtained, which induces and/or increases the immune response of the patient receiving said medicinal product.

This biological agent may in particular be chosen from bacterial, viral, yeast, parasite or fungal antigens, tumor antigens, and autologous and/or heterologous tumor cell lysates. This biological agent may also be a nucleic acid which includes at least one antigen chosen from bacterial, viral, yeast, parasite or fungal antigens and tumor antigens.

For the purpose of the present invention, a tumor antigen is defined as a tumor protein or peptide, and in particular as an epitope, especially a CTL (cytotoxic T lymphocyte) epitope (peptide sequences which interact with class I molecules and which are presented to CD8+ T lymphocytes) or as the nucleic acid sequence encoding this antigen. In a nonlimiting capacity, mention may be made of the following tumor antigens: MAGE-2, MAGE-3, MART, MUC-1, MUC-2, HER-2, GD2, carcinoembryonic antigen (CEA), TAG-72, ovarian-associated antigens OV-TL3 and MOV18, TUAN, alpha-fetoprotein (AFP), OFP, CA-125, CA-50, CA-19-9, renal tumor-associated antigen G250, EGP-40 (or EpCAM), S100 (malignant melanoma-associated antigen), p53, prostate tumor-associated antigens (e.g. PSA and PSMA) and p21ras.

For the purpose of the present invention, the expression "autologous tumor cells" is intended to mean tumor cells belonging to the individual who will receive the medicinal product according to the invention. The expression "heterologous tumor cells" is intended to mean cells derived from tumors originating from an individual other than the individual who will receive the medicinal product according to the invention. The use of heterologous tumor cells makes it possible in particular to obtain a medicinal product for treating patients suffering from cancer from whom it is not possible to take a sample of tumor cells. The tumor cells may be obtained by taking a sample from cancerous tissues, in particular a biopsy or a surgical resection.

For the purpose of the present invention, the term "cell lysate" is intended to mean a mixture of intracellular and/or membrane-bound antigens, obtained according to a cell lysis protocol well known to those skilled in the art, such as in particular by mechanical, chemical or enzymatic lysis of cells.

According to a preferred embodiment of the invention, the medicinal product according to the invention is intended for the treatment and/or prevention of an infection of bacterial, viral, fungal or parasitic origin or an infection caused by a yeast, and/or for the treatment and/or prevention of cancers, i.e. against all diseases due to abnormal cell multiplication, in particular myelomas, lymphomas, leukemias, kidney carcinomas, brain carcinomas, carcinomas of the prostate, rectal carcinomas, colon carcinomas, pancreatic carcinomas, ovarian carcinomas, lung carcinomas, liver carcinomas, breast carcinomas, skin cancers chosen from keratinomas and carcinomas, and melanomas.

The medicinal product according to the invention may in particular be intended for administration orally, for example in the form of a tablet, a gel capsule, a oral solution, etc., rectally, in the form of a suppository, parenterally, in particular in the form of an injectable solution, especially intravenously, intradermally, subcutaneously, or topically, in the form of a cream, ointment or lotions, according to conventional administration protocols well known to those skilled in the art. The medicinal product according to the invention may also comprise a transporting agent for transporting at least one fraction of oxidized lipoproteins chosen from oxidized VLDLs and/or oxidized IDLs and/or oxidized LDLs, in a form which makes it possible to improve its stability and/or its immunostimulatory activity and/or its ability to induce an antitumor immune response. This transporting agent may in particular be in the form of a lipid emulsion, or of a particle of the liposome, microsphere or nanosphere type or any type of structure for encapsulating and presenting said lipoprotein fraction in particulate form.

The dosage depends on the seriousness of the condition and is adjusted so as to obtain a suitable therapeutic treatment.

The present invention also relates to a method for the in vitro differentiation of precursor cells, in particular of monocytes, into mature dendritic cells, according to which precursor cells are provided in a suitable culture medium which allows differentiation thereof, and a predetermined amount of at least one fraction of oxidized lipoproteins chosen from oxidized VLDLs and/or oxidized IDLs and/or oxidized LDLs is added to said medium. Preferably, the precursor cells are monocytes.

The term "suitable medium" is intended to mean a culture medium comprising all the elements required for cell viability. By way of example, mention may be made of the medium RPMI 1640 and derivatives thereof. Preferably, the culture medium comprises agents which induce the differentiation of the precursor cells into immature dendritic cells. Preferably, the culture medium comprises the interleukin IL-4 and the factor GM-CSF (Granulocyte Macrophage Colony-Stimulating factor).

According to a preferred embodiment of the invention, oxidized lipoproteins are added to said medium in vitro, in an amount of in particular between approximately 1 and 20 µg/ml, preferably between approximately 2.5 and 15 µg/ml, and advantageously between approximately 8 and 12 µg/ml. According to a preferred embodiment of the invention, the fraction(s) of oxidized lipoproteins is or are added to said medium between the 1st and 6th day of differentiation of the precursor cells, preferably between the 4th and 5th day of differentiation of the precursor cells. Preferably, the precursor cells are monocytes.

According to another embodiment of the invention, the method also comprises the addition of a biological agent to the culture medium. Preferably, the biological agent is added to the culture medium on D5 or D6.

The invention also relates to the use of said dendritic cells and of at least one biological agent, for producing a medicinal product intended for the treatment and/or prevention of an infection of bacterial, viral, fungal or parasitic origin or an infection caused by yeast, and/or for the treatment and/or prevention of cancers. Thus, in a nonlimiting capacity, it is possible to take a blood sample from a patient suffering from a cancer or from an infectious disease, in order to obtain monocytes. These monocytes are then differentiated into mature dendritic cells obtained according to the method as defined above, in the presence of an antitumor antigen or an antigen from the infectious agent against which it is desired to increase the patient's immune response, which are then used to produce a medicinal product.

The present invention also relates to an activating agent for the differentiation of precursor cells, in particular of monocytes, into mature dendritic cells, comprising at least one fraction of oxidized lipoproteins chosen from oxidized VLDLs and/or oxidized IDLs and/or oxidized LDLs. The term "activating agent" is intended to mean a molecule which, in a pharmaceutical composition, induces the effects of a medication or reinforces or supplements the effects of the main medication. In the case of an immunization composition, the activating agent is an adjuvant which is preferably a molecule which stimulates the immune response of the host organism.

The invention also relates to a pharmaceutical composition comprising a fraction of oxidized lipoproteins chosen from oxidized VLDLs and/or oxidized IDLs and/or oxidized LDLs, and at least one biological agent, in combination with at least one pharmaceutically acceptable excipient. The pharmaceutically acceptable excipient is chosen according to the desired pharmaceutical form and the desired method of administration, and the pharmaceutical composition is obtained according to the principles well known to those skilled in the art in galenics. The pharmaceutical composition according to the invention is intended in particular for the treatment and/or prevention of an infection of bacterial, viral, fungal or parasitic origin or an infection caused by yeast, and/or for the treatment and/or prevention of cancers.

Finally, the invention relates to a method for activating T lymphocytes against a given biological agent, characterized in that:

precursor cells are provided in a suitable culture medium which allows differentiation thereof;

a predetermined amount of at least one fraction of oxidized lipoproteins chosen from oxidized VLDLs and/or oxidized IDLs and/or oxidized LDLs is added to said medium;

at least one biological agent is added to the culture medium; and the mature dendritic cells are cocultured in the presence of T lymphocytes.

Preferably, the precursor cells are monocytes. According to a preferred embodiment of the invention, the activation of the T lymphocytes is carried out in vitro.

The following examples are given by way of explanation and are in no way limiting in nature. They will make it possible to understand the invention more clearly.

EXAMPLE 1

Differentiation of Monocytes in Culture into Dendritic Cells in the Absence of Oxidized LDLs in the Culture Medium Isolation, placing in culture and initiation of the differentiation of monocytes—The monocytes are isolated from human peripheral blood by a first density gradient centrifugation (400 g; 20 minutes) in Ficoll-Hypaque, followed by a second centrifugation (400 g; 20 minutes) in a 50% Percoll solution. The monocytes are then purified by immunomagnetic depletion (Dynal, Oslo, Norway), using a cocktail of anti-CD19 (hybridoma 4G7) (Becton Dickinson, Francklin Lakes, N.J., USA), anti-CD3 (OKT3, American Type Culture Collection, Rockeville, Md.) and anti-CD56 (NKH1, Beckman Coulter, Fullerton, Calif., USA) monoclonal antibodies. The monocytes thus obtained are then purified to at least 90%, as shown by the absence of CD1a and CD14 markers. The differentiation of the monocytes into dendritic cells is initiated with 40 ng/ml of recombined human GM-CSF (Granulocyte Macrophage Colony-Stimulating Factor) and 250 U/ml of recombined human interleukin IL-4.

The monocytes are placed in culture in RPMI 1640 medium (Life Technologies, Rockeville, Md., USA) enriched with 2 mM of glutamine (Life Technologies), 10 mM of Hepes (Life Technologies), 40 ng/ml of gentamycin (Life Technologies) and
  either 10% of fetal calf serum (Biowest, Nuailles, France) (or FCS culture medium)
  or 10% of lipoprotein-depleted fetal calf serum (Sigma, St Quentin-Fallavier, France) (or LPDS culture medium). This medium is chosen in order to operate under optimum conditions for obtaining an effect of the oxidized LDLs.

Phenotype of the cells in culture—The phenotype of the cells in culture 6 days after initiation of monocyte differentiation is analyzed by flow cytometry on a FACSCalibur (Becton Dickinson, Francklin Lakes, N.J., USA) using FITC (fluorescein isothiocyanate)-conjugated anti-CD14, anti-HLA-DR and anti-CD80, and PE (phycoerythrin)-conjugated anti-CD1a, anti-CD83, anti-CD86, anti-CD40 (Beckman Coulter). It is known by those skilled in the art that monocytes preferentially have a CD14+ CD1a− phenotype, immature dendritic cells preferentially have CD14− CD1a+ CD86− phenotype, and mature dendritic cells preferentially have a CD14− CD1a intermediate-CD86+ phenotype.

After culturing for 5 days in the presence of GM-CSF and IL-4, more than 95% of the monocytes in culture exhibit a phenotype comparable to that of immature dendritic cells. The results are comparable when the monocytes are cultured in an FCS medium or in an LPDS medium.

EXAMPLE 2

Differentiation of Monocytes in Culture into Dendritic Cells in the Presence of Oxidized LDLs in the Culture Medium preparation of LDLs—The LDLs (low density lipoproteins: density of between 1.025 and 1.055 g/ml) are isolated from human plasma by centrifugation. The density of the plasma was brought to 1.025 g/ml using NaBr. After a first centrifugation carried out at 100,000 rpm, at a temperature of 4° C. for 4 h (Beckman TL 100 centrifuge), the upper fraction containing the chylomicrons, the VLDLs (very low density lipoproteins) and the IDLs (intermediate density lipoproteins) is eliminated. The density is then adjusted to 1.055 g/ml with NaBr. A second centrifugation is carried out in a manner comparable to the 1st centrifugation described above. The upper fraction containing the LDLs is recovered, dialyzed against a 150 mM NaCl solution containing 2.4 mM EDTA, pH 7.2, at 4° C., and filtered at 0.45 µm and stored in nitrogen.

The protein content of this LDL fraction is determined by the "Coomassie Protein Micro-assay" technique (trade name, Pierce, Rockford, Ill., USA).

The lipid content of this LDL fraction is determined using Cholesterol RTU, Triglycerides enzymatic PAP150 and Phospholipids enzymatic PAP 150 kits (trade names, bioMérieux, Marcy l'Etoile, France).

The analysis shows that the LDLs are composed of 23±1% of proteins (Apo B protein only), 41±4% of cholesterol, 24±1% of phospholipids and 13±4% of triglycerides. The endotoxins present in the fraction are estimated using an E-toxate test (trade name, Sigma, St Quentin-Fallavier, France). The endotoxin concentration is less than 0.6 pg/ml in the final concentration of LDLs or of oxidized LDLs.

LDL oxidation—The LDL concentration is adjusted to 1 mg/ml by diluting in PBS. The EDTA is removed by dialysis against PBS at 4° C. Oxidation with $Cu^{2+}$ is carried out at 37° C. for 24 h by dialysis against a solution of PBS, $CuSO_4$, at 5 µM. The reaction is stopped by adding 40 µM butylated hydroxytoluene (reference. B1378, Sigma, St Quentin-Fallavier, France), and thorough dialysis at 4° C. against PBS containing 100 µM diethylenediaminepentaacetic acid. The degree of oxidation is determined by the production of malondialdehyde measured by the "LPO586 assay" technique (Oxis, Portland, Oreg., USA).

Isolation, placing in culture and initiation of the differentiation of monocytes in the presence of oxidized LDLs—These steps are carried out according to the protocol of example 1, in the presence of oxidized LDLs. For this, 10 µg/ml of oxidized LDLs are added to the FCS or LPDS culture medium on D0, the day on which the monocyte culture is initiated, D1, D2, D3, D4, D5 and D6, corresponding respectively to the 1st, 2nd, 3rd, 4th, 5th and 6th day of culture.

Phenotype of the cells in culture—The phenotype of the cells in culture is analyzed with respect to the presence of CD86 markers according to the protocol of example 1.

six days after initiation of monocyte differentiation when the oxidized LDLs were added on D0, D3, D4, D5
    seven days after initiation of the monocyte differentiation when the oxidized LDLs were added on D6.

The cells obtained by differentiation of the monocytes in FCS and in the presence of oxidized LDLs from D0 express more CD86 marker than the cells obtained by differentiation of the monocytes in the absence of oxidized LDLs. The results regarding the presence of the CD86 marker (expressed in mean fluorescence intensity) expressed by cells in culture in an LPDS medium in the absence (control) or in the presence of 10 µg/ml of oxidized LDLs added on D0, D3, D4, D5 and D6 are given in table 1.

TABLE 1

Expression of the CD86 marker in the absence or in the presence of oxidized LDLs (10 µg/ml) added on D0, D3, D4, D5 or D6

|  | Control | D0 | D3 | D4 | D5 | D6 |
| --- | --- | --- | --- | --- | --- | --- |
| CD86 | 44 | 187 | 178 | 370 | 403 | 173 |

The induction of CD86 expression is optimal on the 4th or on the 5th day of monocyte differentiation and is dependent on the dose of oxidized LDLs added, as represented in table 2.

TABLE 2

Expression of the CD86 marker in the absence or in the presence of oxidized LDLs at a concentration of 2.5, 5 or 10 µg/ml, added on D5

|  | Control | 2.5 | 5 | 10 |
| --- | --- | --- | --- | --- |
| CD86 | 100 | 195 | 336 | 528 |

In addition, in LPDS medium, the addition of oxidized LDLs on D0 and, more notably on D5, to the culture medium of monocytes undergoing differentiation induces a phenotype characteristic of mature dendritic cells, observed using the markers CD83, CD80, CD86, MHC class II and CD40, in comparison with the monocytes in culture in the absence of oxidized LDLs (control) (table 3).

TABLE 3

Expression of the CD83, CD80 and CD86 markers in the absence (control) or in the presence of oxidized LDLs (10 µg/ml) added on D0 or D5

|  | CD83 | CD80 | CD86 |
| --- | --- | --- | --- |
| Control | 3.3 | 7.5 | 44 |
| D0 | 6.3 | 4.6 | 187 |
| D5 | 20.6 | 16.2 | 403 |

After culturing for 6 days in the presence of GM-CSF and IL-4, and of LDLox, added in particular between the 4th and 5th day of differentiation, the cells obtained exhibit a phenotype comparable to that of mature dendritic cells.

EXAMPLE 3

Differentiation of Monocytes in Culture into Dendritic Cells in the Presence of Nonoxidized LDLs and/or Oxidized LDLs in the Culture Medium The protocol used in this example is comparable to that given in example 2.

Thus, the cells presented in this example are obtained after 6 days of monocyte differentiation in LPDS medium carried out in the absence of oxidized LDLs (according to the protocol of example 1), in the presence of nonoxidized LDLs (50 μg/ml; preparation according to the protocol described in example 2), added to the culture medium on the 5th day of monocyte differentiation, in the presence of oxidized LDLs (10 μg/ml; preparation according to the protocol described in example 2), added to the culture medium on the 5th day of monocyte differentiation, in the presence of oxidized LDLs (10 μg/ml) and nonoxidized LDLs (50 μg/ml), added to the culture medium on the 5th day of monocyte differentiation.

Phenotype of the cells in culture—The phenotype of the cells in culture is analyzed with respect to the presence of the CD86 marker according to the protocol of example 1, six days after initiation of monocyte differentiation. The results are given in table 4.

TABLE 4

Expression of the CD86 marker in the absence or in the presence of oxidized LDLs, of nonoxidized LDLs, and of oxidized LDLs and nonoxidized LDLs

|  | Control | LDL ox | LDL | LDL + LDLox |
|---|---|---|---|---|
| CD86 | 53 | 439 | 79 | 232 |

Thus, the nonoxidized LDLs added to the culture medium on D5 have no effect on the expression of the CD86 marker, suggesting that, unlike the oxidized LDLS, the nonoxidized LDLs have no effect on the differentiation of monocytes into mature dendritic cells. Furthermore, an excess of nonoxidized LDLs in the culture medium blocks the action of the oxidized LDLs on the differentiation of monocytes into mature dendritic cells.

After culturing for 6 days in the presence of GM-CSF and IL-4, and of nonoxidized LDLs or of nonoxidized LDLs in excess with respect to the oxidized LDLs, added in particular between the 4th and 5th day of differentiation, the cells obtained exhibit a phenotype similar to that of immature dendritic cells.

EXAMPLE 4

Internalization Capacity of the Cells Obtained by Differentiation of Monocytes in the Absence or in the Presence of Oxidized LDLs in the Culture Medium The cells are obtained after 6 days of monocyte differentiation in LPDS medium carried out in the absence of oxidized LDLs (according to the protocol of example 1)

in the presence of 10 μg/ml of oxidized LDLs added to the culture medium on the 5th day of monocyte differentiation (D5, according to the protocol of example 2).

On the 6th day of culturing, the cells are resuspended in an FCS culture medium and incubated at 37° C.:

for 30 minutes with 1 mg/ml of FITC-T70-Dextran (Sigma) in order to estimate the capacity of these cells for internalization by receptor-mediated endocytosis;

for 30 minutes with 1 mg/ml of Lucifer Yellow (ref. L0259, Sigma, St Quentin-Fallavier, France) in order to estimate the capacity of these cells for internalization by pinocytosis;

for 3 hours with carboxylate-modified yellow-green Fluo-Spheres (trade name, 0.45 μm, Molecular Probes, Leiden, The Netherlands) in order to estimate the capacity of these cells for internalization by macropinocytosis.

The internalization is stopped on ice with a cold PBS buffer containing 1% BSA (Bovine Serum Albumin) and 0.05% $NaN_3$. The cells are washed 3 times at 4° C. in this same buffer and the fluorescence is quantified by FACScalibur (trade name, Becton Dickinson).

As shown in table 5, the capacity for internalization by endocytosis, pinocytosis and macropinocytosis are greatly decreased when 10 μg/ml of oxidized LDLs are added to the culture medium on D5, compared to the control performed in the absence of oxidized LDLs.

TABLE 5

Capacity for internalization by endocytosis, pinocytosis and macropinocytosis of the monocytes differentiated in the absendce (control) or in the presence of oxidized LDLs (10 μg/ml added on D5)

|  | Endocytosis | Pinocytosis | Macropinocytosis |
|---|---|---|---|
| Control | 100% | 100% | 100% |
| 10 μg/ml of LDL ox | 41% | 39% | 54% |

A reduction in internalization capacities is one of the characteristics of mature dendritic cells. It should be noted that the cells obtained in the presence of nonoxidized LDLs or of nonoxidized LDLs in excess with respect to the oxidized LDLs do not exhibit this decrease in internalization capacities, suggesting that the cells thus obtained are not mature dendritic cells.

These results show that, in the presence of oxidized LDLs, added on the 5th day of differentiation, the monocytes have a strong tendency to differentiate into cells exhibiting the functional characteristics of mature dendritic cells.

EXAMPLE 5

Quantification of the Secretion of Cytokines by the Cells Obtained by Differentiation of Monocytes in the Absence or in the Presence of Oxidized LDLs The cells are obtained after 6 days of monocyte differentiation in LPDS carried out in the absence of oxidized LDLs (protocol of example 1), in the presence of 10 μg/ml of oxidized LDLs added to the culture medium on the 5th day of monocyte differentiation (D5, protocol of example 2).

The presence of cytokines, in particular the interleukins IL10 (anti-inflammatory cytokine) and IL12p70 (pro-inflammatory cytokine) secreted by mature dendritic cells, is determined using an ELISA kit specific for cytokines (Endogen, Woburn, Mass., USA). The results are given in table 6.

TABLE 6

Secretion of cytokines by the monocytes differentiated in the absence (control) or in the presence of oxidized LDLs (10 μg/ml, added on D5)

| Secretion of cytokines (pg/ml) | IL10 | IL12p70 |
|---|---|---|
| Control | 12 ± 1 | 9 ± 11 |
| 10 μg/ml of LDL ox | 17 ± 8 | 159 ± 24 |

The cells obtained by differentiation of the monocytes in the presence of oxidized LDLs added to the culture medium on the 5th day of monocyte differentiation acquired the ability to secrete the interleukin IL12p70 compared to the cells obtained by differentiation of the monocytes in the absence of oxidized LDLs (control), which interleukin is one of the cytokines mainly secreted by mature dendritic cells. IL10 secretion is not obtained under any of the conditions.

These results show a greater tendency of the monocytes to differentiate directly into cells exhibiting a phenotype and a functionality comparable to those of mature dendritic cells when oxidized LDLs are added on the 5th day of differentiation.

EXAMPLE 6

Ability of the Cells Obtained by Differentiation of Monocytes in the Absence or in the Presence of Oxidized LDLs to Stimulate T Lymphocytes The cells are obtained after 6 days of monocyte differentiation in LPDS culture medium carried out in the absence of oxidized LDLs, in an LPDS culture medium according to the protocol of example 1;

in the presence of 10 µg/ml of oxidized LDLs added to an LPDS culture medium on the 5th day of monocyte differentiation (D5, protocol of example 2).

Naïve T lymphocytes are isolated from human peripheral blood. Peripheral blood mononuclear cells are isolated by density gradient centrifugation (400 g, 20 minutes) in the presence of Ficoll-Hypaque. After monocyte depletion on a Percoll gradient, the peripheral blood lymphocytes are located in the dense fraction. The T lymphocytes are purified by immunomagnetic depletion using a cocktail of anti-CD19 (antibody 4G7), anti-CD16 (antibody 3G8), anti-CD56 (antibody NKH1), anti-glycophorin A (antibody 11E4B7.6) and anti-CD14 (antibody RMPO52) monoclonal antibodies sold by Beckman Coulter.

The purified T lymphocytes, as shown by the presence of the CD3 marker, are cultured in flat-bottomed 96-well culture plates with the antigen-presenting cells. The term "antigen-presenting cells" is intended to mean monocytes differentiated in the presence or absence of oxidized LDLs. $2 \times 10^5$ allogenic or syngenic T cells are cultured in 200 µl of culture medium according to an antigen-presenting cells/T cell ratio of 1:5, 1:10 or 1:20. After 4 days, 50 µl of the culture supernatant are used to determine IL-2 (interleukin 2) secretion with an ELISA kit (Endogen, Woburn, Mass., USA), and are replaced with 50 µl of a medium containing 1 µCi of [$^3$H]-thymidine. After culturing for 16 h, the cells are collected on filter paper and the thymidine incorporation, reflecting T lymphocyte proliferation, is measured using a Matrix 9600 Direct beta counter (trade name, Packard, Meriden, Conn., USA).

a) Interleukin 2 (IL-2) Secretion

As shown in table 7, IL2 secretion by the allogenic T lymphocytes (expressed conventionally according to the dendritic cell/T lymphocyte ratio, DC/LT ratio) is induced when the dendritic cells originate from the differentiation of monocytes in the presence of oxidized LDLs added on D5, in comparison with the results obtained in the absence of oxidized LDLs (control).

TABLE 7

Stimulation of IL2 secretion by allogenic T lymphocytes (according to the DC/LT ratio) induced by monocytes differentiated in the absence (control) or in the presence of oxidized LDLs (10 µg/ml, added on D5)

| | DC/LT ratio | | | |
|---|---|---|---|---|
| | 0 | 0.05 | 0.1 | 0.2 |
| Control | 0 | 72 | 64 | 84 |
| 10 µg/ml of LDL ox | 0 | 189 | 373 | 454 |

These results show an increase in the allostimulation capacities of the cells obtained after differentiation of the monocytes in the presence of oxidized LDLs.

b) T Lymphocyte Proliferation

As shown in table 8, allogenic T lymphocyte proliferation, estimated by $^3$H-thymidine incorporation, induced by the antigen-presenting cells is greatly increased when these cells are obtained by differentiation of the monocytes in the presence of oxidized LDLs on D5, compared with the results obtained in the absence of oxidized LDLs (control). This effect is dependent on the dose of oxidized LDLs present in the culture medium (2.5, 5 or 10 µg/ml).

TABLE 8

Incorporation of $^3$H-thymidine (counts per minute) by allogenic T lymphocytes induced by monocytes differentiated in the absence (control) or in the presence of oxidized LDLs at a concentration of 2.5, 5 or 10 µg/mL, added on D5

| | Control | 2.5 | 5 | 10 |
|---|---|---|---|---|
| $^3$H-thymidine | 11712 ± 2476 | 13650 ± 1703 | 14906 ± 3387 | 25010 ± 1754 |

The monocytes differentiated in the presence of oxidized LDLs (10 µg/ml) on D5 are also capable of inducing syngenic T lymphocyte proliferation much more effectively than the monocytes differentiated in the absence of oxidized LDLs (control), i.e. conventional immature dendritic cells, as shown in table 9.

TABLE 9

Incorporation of $^3$H-thymidine (counts per minute) by synergenic T lymphocytes induced by monocytes differentiated in the absence (control) or in the presence of oxidized LDLs (10 µg/ml) added on D5

| | Control | 10 µg/ml of LDL ox |
|---|---|---|
| $^3$H-thymidine | 920 ± 331 | 2983 ± 501 |

These results indicate that the oxidized LDLs promote the production of cells capable of presenting peptides originating from the degradation of internalized exogenous proteins, which cells, as a result, exhibit functional characteristics of mature dendritic cells. It should be noted that the ability to present peptides is not observed when the cells are obtained from monocytes cultured in the presence of nonoxidized LDLs or of nonoxidized LDLs in excess with respect to the oxidized LDLs, as obtained according to the protocol of example 2.

EXAMPLE 7

Primary Activation of T Lymphocytes Specific for Hepatitis C Virus Protease by Mature Dendritic Cells Obtained According to the Invention The dendritic cells used in this example are prepared according to the protocol of example 3, in the presence of the NS3 antigen of the hepatitis C virus protease. After 6 days of monocyte differentiation in the presence of oxidized LDLs (10 µg/ml) and/or of nonoxidized LDLs (50 µg/ml), added on D5 to the culture medium, the cells thus obtained are cocultured for 5 days in the presence of the NS3 antigen of the hepatitis C virus protease, and:
- of total T lymphocytes, obtained according to the protocol of example 5, or
- of CD 4+ T lymphocytes, obtained according to the protocol of example 5, with the variation consisting in adding an anti-CD8 antibody (Beckman Coulter) to the cocktail of monoclonal antibodies (Beckman Coulter) during the depletion.

The secretion of gamma interferon by total T lymphocytes or CD4+T lymphocytes, representative of a Th1-type response, is then measured (ELISA kit (Endogen, Woburn, Mass., USA)).

The results obtained on the total T lymphocytes are given in table 10 and the results obtained on the CD4+T lymphocytes are given in table 11.

TABLE 10

Secretion of gamma-interferon (pg/ml) by syngenic T lymphocytes specific for the NS3 antigen and activated by cells obtained by differentiation of monocytes in the presence of oxidized LDLs, of nonoxidized LDLs, or of oxidized LDLs + nonoxidized LDLs

| NS3 (µg/ml) | Control | LDLox | LDL | LDLox + LDL |
|---|---|---|---|---|
| 0 | 14 ± 6 | 24 ± 9 | 17 ± 5 | 44 ± 21 |
| 100 | 122 ± 39 | 723 ± 388 | 139 ± 113 | 112 ± 94 |

These results suggest that the total lymphocytes present, cocultured in the presence of mature dendritic cells obtained by differentiation of monocytes in the presence of oxidized LDLs, have developed an increased ability to secrete gamma-interferon, defining a Th1 type immune response directed against the NS3 antigen of the hepatitis C virus.

TABLE 11

Secretion of gamma interferon (pg/ml) by CD4 + T lymphocytes specific for the NS3 antigen and activated by cells obtained by differentiation of monocytes in the presence of oxidized LDLs, of nonoxidized LDLs, or of oxidized LDLs + nonoxidized LDLs

| NS3 (µg/ml) | Control | LDLox | LDLox + LDL |
|---|---|---|---|
| 0 | 3 ± 2 | 5 ± 4 | 4 ± 3 |
| 100 | 43 ± 40 | 809 ± 180 | 84 ± 50 |

These results suggest that the CD4+lymphocytes cocultured in the presence of mature dendritic cells obtained by differentiation of monocytes in the presence of oxidized LDLs have developed an increased ability to secrete gamma-interferon, defining a Th1-type immune response directed against the NS3 antigen of the hepatitis C virus.

These results suggest that the dendritic cells obtained in the presence of oxidized LDLs are capable of inducing a primary T response, which is an essential property of an adjuvant.

In conclusion, the addition of oxidized LDLs to the culture medium makes it possible to obtain, from monocytes, dendritic cells exhibiting the characteristics of mature dendritic cells, in particular with regard to their reduced capacity for endocytosis and their ability to stimulate allogenic T lymphocytes and to activate naïve syngenic T lymphocytes specific for an antigen. These results are not obtained when nonoxidized LDLs are added to the culture medium, and the addition to the culture medium of nonoxidized LDLs in excess blocks the effects of the oxidized LDLs on the differentiation of monocytes into mature dendritic cells. It should be noted, however, that the cells obtained according to the invention also exhibit their own specific characteristics, in particular in terms of the secretion of certain cytokines.

The invention claimed is:

1. A method for the in vitro differentiation of precursor cells into mature dendritic cells, comprising:
    a) providing precursor cells in a suitable medium, that allows differentiation of the precursor cells; and
    b) adding a predetermined amount of at least one fraction of oxidized lipoproteins selected from the group consisting of: oxidized very low density lipoproteins (VLDLs), oxidized intermediate density lipoproteins (IDLs), oxidized low density lipoproteins (LDLs), and mixtures thereof to said medium such that the cultured precursor cells differentiate into mature dendritic cells.

2. The method as claimed in claim 1, wherein the precursor cells are monocytes.

3. The method as claimed in claim 1, wherein the at least one fraction of oxidized lipoproteins is a fraction of oxidized LDLs.

4. The method as claimed in claim 1, wherein the at least one fraction of oxidized lipoproteins is added to said medium in an amount between approximately 1 and 20 µg/ml.

5. The method as claimed in claim 4, wherein the at least one fraction of oxidized lipoproteins is added to said medium in an amount between approximately 2.5 and 15 µ/ml.

6. The method as claimed in claim 5, wherein the at least one fraction of oxidized lipoproteins is added to said medium in an amount between 8 and 12 µ/ml.

7. The method as claimed in claim 1, wherein the at least one fraction of oxidized lipoproteins is added to said medium between the 3rd and 6th day of differentiation of the precursor cells.

8. The method as claimed in claim 7, wherein the at least one fraction of oxidized lipoproteins is added to said medium between the 4th and the 5th day of differentiation of the precursor cells.

9. The method as claimed in claim 1, wherein a biological agent is also added to the culture medium.

10. A method for activating T lymphocytes in vitro, comprising:
    a) providing precursor cells in a suitable medium, that allows differentiation of the precursor cells;
    b) adding a predetermined amount of at least one fraction of oxidized lipoproteins selected from the group consisting of: oxidized very low density lipoproteins (VLDLs), oxidized intermediate density lipoproteins (IDLs), oxidized low density lipoproteins (LDLs), and mixtures thereof to said medium such that the cultured precursor cells differentiate into mature dendritic cells;

c) adding at least one biological agent to the culture medium; and d) coculturing the mature dendritic cells in the presence of T lymphocytes.

11. A method for producing a medicinal product for treating a bacterial, viral, fungal, yeast, or other parasitic infection, comprising:

a) culturing precursor cells in a medium that allows differentiation of the precursor cells;

b) adding a predetermined amount of at least one fraction of oxidized lipoproteins selected from the group consisting of: oxidized very low density lipoproteins (VLDLs), oxidized intermediate density lipoproteins (IDLs), oxidized low density lipoproteins (LDLs), and mixtures thereof to said medium, wherein the predetermined amount is sufficient to cause the precursor cells to differentiate into mature dendritic cells;

c) adding a predetermined amount of at least one biological agent to said medium; and d) recovering the mature dendritic cells, wherein the mature dendritic cells present antigens to the at least one biological agent.

12. The method as claimed in claim 11, wherein the precursor cells are monocytes.

13. The method as claimed in claim 11, wherein the at least one fraction of oxidized lipoproteins consists of a fraction of oxidized LDLs.

14. The method as claimed in claim 11, wherein the biological agent is selected from the group consisting of: bacterial antigens, viral antigens, yeast antigens, fungal antigens, and other parasitic antigens.

15. The method as claimed in claim 11, wherein the biological agent is nucleic acid encoding at least one antigen selected from the group consisting of: bacterial antigens, viral antigens, yeast antigens, fungal antigens, and other parasitic antigens.

16. A method for producing a medicinal product for treating cancer, comprising:

a) culturing precursor cells in a medium that allows differentiation of the precursor cells;

b) adding a predetermined amount of at least one fraction of oxidized lipoproteins selected from the group consisting of: oxidized very low density lipoproteins (VLDLs), oxidized intermediate density lipoproteins (IDLs), oxidized low density lipoproteins (LDLs), and mixtures thereof to said medium, wherein the predetermined amount is sufficient to cause the precursor cells to differentiate into mature dendritic cells;

c) adding a predetermined amount of at least one biological agent to said medium; and d) recovering the mature dendritic cells, wherein the mature dendritic cells present antigens to the at least one biological agent.

17. The method as claimed in claim 16, wherein the precursor cells are monocytes.

18. The method as claimed in claim 16, wherein the at least one fraction of oxidized lipoproteins consists of a fraction of oxidized LDLs.

19. The method as claimed in claim 16, wherein the biological agent is selected from the group consisting of: tumor antigens, autologous tumor cell lysates, heterologous tumor cell lysates, and a mixture of autologous and heterologous tumor cell lysates.

20. The method as claimed in claim 16, wherein the biological agent is nucleic acid encoding at least one antigen selected from the group consisting of: tumor antigens, autologous tumor cell lysates, heterologous tumor cell lysates, and a mixture of autologous and heterologous tumor cell lysates.

* * * * *